United States Patent
North

(10) Patent No.: US 10,035,012 B2
(45) Date of Patent: Jul. 31, 2018

(54) PERCUTANEOUS ELECTRODE

(76) Inventor: Richard B. North, Baltimore, MD (US)

( * ) Notice: Subject to any disclaimer, the term of this patent is extended or adjusted under 35 U.S.C. 154(b) by 1192 days.

(21) Appl. No.: 13/640,616

(22) PCT Filed: Feb. 21, 2011

(86) PCT No.: PCT/US2011/025588
§ 371 (c)(1),
(2), (4) Date: Jan. 16, 2013

(87) PCT Pub. No.: WO2011/103530
PCT Pub. Date: Aug. 25, 2011

(65) Prior Publication Data
US 2013/0110210 A1    May 2, 2013

Related U.S. Application Data

(60) Provisional application No. 61/306,561, filed on Feb. 22, 2010.

(51) Int. Cl.
*A61N 1/05* (2006.01)
*A61B 17/34* (2006.01)
*A61M 25/01* (2006.01)

(52) U.S. Cl.
CPC ......... *A61N 1/0553* (2013.01); *A61N 1/0551* (2013.01); *A61B 17/3468* (2013.01); *A61M 25/0152* (2013.01)

(58) Field of Classification Search
CPC ...... A61N 1/05; A61N 1/0504; A61N 1/0551; A61N 1/0553; A61N 1/0558; A61N 1/056; A61N 1/057; A61N 2001/058
USPC .................. 607/116, 117, 119, 125
See application file for complete search history.

(56) References Cited

U.S. PATENT DOCUMENTS

| | | |
|---|---|---|
| 4,379,462 A | 4/1983 | Brokan et al. |
| 4,660,571 A | 4/1987 | Hess et al. |
| 4,800,898 A | 1/1989 | Hess et al. |
| 5,458,629 A | 10/1995 | Baudino et al. |
| 5,728,149 A | 3/1998 | Laske et al. |
| 5,733,322 A | 3/1998 | Starkebaum |

(Continued)

FOREIGN PATENT DOCUMENTS

WO    2005/105201    11/2005

OTHER PUBLICATIONS

Miyazawa, Gabriela, et al. "Differential Effects of Spinal Cord Stimulation Are Achieved with Three-Lead Patterns." Medtronic Neuromodulation. Minneapolis, MN, USA. http://professional.medtronic.com/wcm/groups/mdtcom_sg/@mdt/@neuro/documents/documents/scs-3lead-chart.pdf. Retrieved Dec. 7, 2010.

*Primary Examiner* — George Evanisko
(74) *Attorney, Agent, or Firm* — Whiteford, Taylor & Preston, LLP; Gregory M. Stone

(57) ABSTRACT

Disclosed is a system including an electrode and a stylet configured to steer the electrode towards its intended position during implantation, and a method for such system's use. An electrode is provided having regions with varied flexibility. A stylet having bends that are indexed to specific regions of flexibility of the electrode may be inserted into the electrode, and upon minimal radial and/or longitudinal movement of the stylet within the electrode, will cause the magnitude of the angle to which the lead is bent to either increase or decrease so as to aid the operator in placement of the electrode.

15 Claims, 7 Drawing Sheets

(56) References Cited

U.S. PATENT DOCUMENTS

| | | |
|---|---|---|
| 5,807,339 A | 9/1998 | Bostroem et al. |
| 6,066,165 A | 5/2000 | Racz |
| 6,070,104 A * | 5/2000 | Hine et al. .................... 607/123 |
| 6,246,914 B1 | 6/2001 | de la Rama et al. |
| 6,493,590 B1 | 12/2002 | Wessman et al. |
| 6,510,347 B2 | 4/2003 | Borkan |
| 6,553,264 B2 | 4/2003 | Redko et al. |
| 6,895,283 B2 * | 5/2005 | Erickson et al. ............ 607/117 |
| 7,047,082 B1 | 5/2006 | Schrom et al. |
| 7,072,719 B2 | 7/2006 | Vinup et al. |
| 7,229,405 B2 | 6/2007 | Lau et al. |
| 7,239,923 B1 * | 7/2007 | Tockman et al. ............ 607/119 |
| 7,359,755 B2 | 4/2008 | Jones et al. |
| 7,590,454 B2 | 9/2009 | Garabedian |
| 2002/0022873 A1 | 2/2002 | Erickson et al. |
| 2002/0065544 A1 * | 5/2002 | Smits ........................... 607/122 |
| 2004/0162601 A1 * | 8/2004 | Smits ........................... 607/125 |
| 2005/0203599 A1 | 9/2005 | Garabedian et al. |
| 2007/0213795 A1 * | 9/2007 | Bradley et al. ............... 607/116 |
| 2007/0225784 A1 | 9/2007 | Bly et al. |
| 2009/0005844 A1 | 1/2009 | Swoyer et al. |
| 2009/0105724 A1 | 4/2009 | Yoshizaki |
| 2009/0198312 A1 | 8/2009 | Barker |
| 2009/0204192 A1 | 8/2009 | Carton et al. |
| 2010/0179562 A1 | 7/2010 | Linker et al. |
| 2010/0228330 A1 * | 9/2010 | Bornzin ....................... 607/122 |

* cited by examiner

PERCUTANEOUS ELECTRODE

TECHNICAL FIELD

The present invention relates generally to the field of implantable electrodes, and more particularly to a system including an electrode and a stylus configured to steer an electrode toward its intended position during implantation.

BACKGROUND ART

Percutaneous electrodes were introduced in the 1970's as a minimally invasive technique to deliver spinal cord stimulation (SCS), so as to screen patients for satisfactory responses before implanting permanent electrodes via laminectomy. The technique was quickly adapted for chronic implantation, and since the 1980's the majority of permanent systems have used percutaneous rather than laminectomy electrodes.

Percutaneous SCS electrodes are inserted into the epidural space through a Tuohy type needle, bent at its tip to allow the electrode to emerge at an angle and then ascend cephalad, in or parallel to the midline. Since the early 1980's they have had multiple contacts, forming a linear electrode array. Two or more can be placed in parallel to form a two-dimensional array. Insertion is guided by intraoperative fluoroscopy and by test stimulation as the electrode is advanced in the epidural space. The tip of the advancing electrode is bent at an angle so that it may be steered as it advances by rotating it, moving the tip from right to left. Right-left positioning is critical, to such an extent that a well-placed midline electrode placed percutaneously was seen to outperform two electrodes placed side by side, in a series of controlled trials performed at Johns Hopkins Hospital from 2003-2005. In engineering terms, the system (patient and stimulator) resolves smaller dimensions than the width of standard percutaneous electrodes, such that simply placing more electrode contacts does not substitute for precise placement.

Anterior-posterior position (in front of or behind dorsal epidural fat) is important, as well—not only because proximity of the electrodes to the spinal cord increases efficiency and selectivity (of dorsal columns vs. dorsal roots), but also because recruitment of small pain fibers in ligamentum flavum (behind epidural fat) commonly causes painful side effects, and one way to mitigate them is to keep the electrode in front of epidural fat and in direct contact with the dura. An experienced operator will attempt to keep track of which way the tip of the advancing electrode is pointing, even on monoplanar (anterior-posterior) fluoroscopy, and attempt to direct the tip of the electrode from right to left and from front to back.

Where SCS is to be administered by less experienced practitioners, multiple electrodes will often be used to bracket or "carpet bomb" the target area. Most (70-80%) percutaneous systems currently implanted have dual electrodes—in part for this reason, and in part to provide redundancy—the demonstrable inferiority of dual lead systems for common low back conditions notwithstanding. The best use of this technology may in fact be to place triple electrodes, which offer potential advantages whether they are placed perfectly, or by experienced hands (taking advantage of transverse tripole capabilities) or imperfectly (simply offering redundancy).

In any of the above settings, and whether in experienced or inexperienced hands, percutaneous SCS electrode steerability is very important, and none of the presently available products address it adequately. Not only must the electrode be steerable, but the steering must also be variable. More particularly, major steering input is required as the electrode emerges from the tip of a Tuohy or similar needle, which necessarily is not parallel to the epidural space as seen in the sagittal plane. The electrode must negotiate a bend; if it does not bend sufficiently, it may indent the dura (or even the spinal cord). If it deviates to one side, it will still tend to continue ventrally, into the "gutter" in the lateral epidural space. Not only is there a bend in the sagittal plane, there is often one in the coronal plane, as the needle generally is not parallel to the midline, as it is inserted off the midline to avoid the spinous processes. Thus, as the electrode emerges it tends to deviate laterally, to one side or the other, and once it has done so it may not be possible to steer it back to the midline. An analogy may be made with descending a steep "on ramp" onto an icy highway which has a high crown in the center of the road and deep gutters on either side.

Once having deviated substantially from the midline, even if it is steered back, as seen on A-P fluoroscopy, the electrode may end up ventral to the spinal cord and dura, and this may not be appreciated without changing to a lateral fluoroscopic view.

Minor steering inputs are required after the electrode has negotiated the bend at the tip of the Tuohy needle and is ascending in the midline. The large bend which was an asset in negotiating the initial turn becomes a liability, as relatively small right-left adjustments are made as the electrode is advanced to its final position. Pointing a large bend to the left or right causes major unwanted deviations to either side; pointing it dorsally tends to engage dorsal ligamentous structures and webs, at the same time moving it away from the spinal cord. Pointing it ventrally, so that it slides along the dura, pushes the dura anteriorly; this tends to be unstable, and the electrode tip may rotate and jump to one side or the other. Furthermore, when the electrode is curved significantly in the sagittal plane its contacts are at different distances from the spinal cord, and stimulation thresholds vary substantially. This frustrates test stimulation to guide placement.

Since they were first introduced in the 1970's, all percutaneous SCS electrodes have consisted of rigid cylindrical metal contacts on flexible catheters (for example silicone elastomer, polyethylene, and more recently polyurethane). The flexible catheter, within which are electrical conductor (s) to the electrode contact(s), accommodates bending, allowing for example insertion through a Tuohy needle with a bend at the tip, so that the advancing assembly can negotiate the bend. The rigid contacts must negotiate the bend in the needle first, and as they increase in length it becomes all the more difficult to negotiate this bend, and then to steer to the target beyond.

As shown in the top view FIG. 1, a typical current, commercially available percutaneous electrode assembly ("lead") 10 has a removable, malleable stylet 20, which may be inserted within the body of the flexible, hollow lead 10. A bend in the stylet 20 causes the lead 10 around it to bend correspondingly. The stylet 20 typically is bent at the tip—indeed, most models come with a bend already in place—and typically the stylet may be inserted all the way to the tip of the lead 10, and to the most distal electrode contact, so that the tip of the lead 10 and the electrode contacts assume a bend. The distal end of the lead 10 has a plurality of rigid electrode contacts 12, and flexible spacer portions 13 between the contacts 12. As the bent tip is advanced under fluoroscopic guidance it can be steered by rotating the stylet 20 and/or the lead 10 so that the advancing tip deviates to the left and the right, dorsally and ventrally, etc. As the bent tip is advanced, as seen on A-P fluoroscopy, rotating it allows it to be steered. Not only can it be steered right-left, it can also be steered dorsal-ventral if the operator follows it on lateral as well as A-P fluoroscopy (and/or keeps mental track of its orientation using the A-P view alone). The electrode tip is most easily steered if it responds in a linear fashion to rotation by the operator at the other end of the lead. Further, as shown in the bottom view of FIG. 1, the bend in stylet 20 may be advanced into and withdrawn from lead 10 so as to modify the extent to which lead 10 bends. If the stylet 20 is not inserted fully within the lumen of lead 10, the bend of stylet 20 is located proximal to the distal end of lead 10, resulting in a larger bend of lead 10 while the tip of lead 10 lacks stiffening and, thus, remains flexible.

Most stylets are coated with Teflon, which facilitates removal and replacement, as is often necessary to change the bend at the tip. It is typically necessary to increase the bend to negotiate the sharp turn at the tip of the needle, as the tip of the electrode enters the epidural space and must be steered to (or back to) the midline; once this has been achieved, a large bend becomes a liability, as noted. The only way to reduce the bend is to withdraw the stylet and replace it—after straightening it, or substituting another stylet with a smaller bend. This is cumbersome, and it can be challenging for the operator to thread the stylet back into the tiny lumen of the lead. Some leads resist this maneuver, and on occasion it becomes necessary to ask for a new lead—which means withdrawing the existing lead and giving up the position achieved so far.

Electrode steerability is best if the curved electrode tip is seen on fluoro and felt by the operator's hand to move in a linear 1:1 fashion as the stylet emerging from the end of the lead assembly is rotated by the operator's hand. A right-handed operator will generally rotate the stylet (which may rotate within the lead) or the stylet/lead assembly (which may rotate together) with his/her left hand, as the thumb and index fingertip of the right hand advance and withdraw the body of the lead as it emerges from the hub of the Tuohy needle in the epidural space. Some Seldinger wire lead blanks achieve this, but no electrode assembly does so; to varying degrees they lag, jump, and sometimes seem to wind up, as though lacking in torsional rigidity.

The malleable stylet may rotate in unison with the "lead" around it, or it may rotate within the lead, or it may (and commonly does, to varying degrees) do both. One presently available device may be clipped to the end of the lead so that the two necessarily rotate together (at least within and adjacent to the clip; they may decouple farther away.) This incurs friction between the outside of the lead, along its length within the needle and the patient; the friction is cumulative as the lead is advanced, and ultimately the stylet begins to rotate within the lead, thus impeding steerability. Rotation and translation of the tip no longer track operator inputs 1:1.

Other presently available devices may have a knob at the end of the stylet, but no clip secures it to the lead; the stylet is unconstrained and can rotate within the lead. The tip of the stylet may engage a bearing within the lead tip in order to reduce friction. As the length of the lead and stylet assembly increases, however, the cumulative drag or friction between the outside of the stylet and the inside of the lead body can become significant, so that the lead tip no longer tracks operator inputs faithfully, 1:1.

Other problems and idiosyncrasies are introduced by assembly and packaging of some available devices. For instance, if the metal stylet inside the plastic lead body is bent, then the plastic lead tends to take a "set" which remains, if only temporarily, after withdrawal of the stylet. This can be useful during implantation, in that it provides finer control over steering, but it then becomes a liability: the lead retains this bend following implantation, and so it may curve left-right, or dorsal-ventral. With time, the curve may straighten out, with unpredictable results.

Moreover, the "set" in the plastic and the bend in the stylet are, of course, pointing in the same direction when the assembly is removed from the package, and they remain so unless disturbed. It is very common, however, to withdraw the stylet at least in part during placement, and if this is done it may not be in phase with the lead, i.e. pointing in the same direction, when the stylet is re-inserted. Sometimes the stylet is removed and replaced, e.g. with a stiffer one, or one with a different bend. In To the inventor's knowledge, there is no provision to address this in any existing product. Marking the stylet and the lead in order to allow alignment would be possible, but they may not be rigid in torsion, and so this might not be reliable.

Still further, the "set" in the plastic lead is, on balance, a liability. Current potential solutions include preassembling with a straight stylet, and allowing the user bend it as desired, or furnishing the stylet separately. Presently available packages include leads that are shipped with a bent stylet in place, incurring the above problem.

DISCLOSURE OF INVENTION

Disclosed is a system including an electrode and a stylet configured to steer the electrode towards its intended position during implantation, and a method for such system's use. An electrode is provided having regions with varied flexibility. A stylet having bends that are indexed to specific regions of flexibility of the electrode may be inserted into the electrode, and upon minimal radial and/or longitudinal movement of the stylet within the electrode, will cause the magnitude of the angle to which the lead is bent to either increase or decrease so as to aid the operator in placement of the electrode.

With regard to certain aspects of a particularly preferred embodiment, a system is provided for positioning a lead within a patient, the system comprising a lead having a shaft with at least two electrode contacts disposed on the shaft and a flexible spacer portion between each of the electrode contacts, and a stylet lumen extending into the lead from a proximal end of the lead towards a distal end of the lead, along with a stylet having a plurality of bends and relatively straight portions extending between the bends, wherein the bends are positioned a distance apart from one another so as to simultaneously align with the flexible spacer portions of the lead when the stylet is positioned within the stylet lumen.

With regard to other aspects of a particularly preferred embodiment, a method of using such system is provided that comprises the steps of inserting the stylet into the stylet lumen toward the distal end of the lead a sufficient distance so that at least one of the bends in the stylet is aligned with at least one of the electrode contacts, moving the lead within a patient in a first direction, moving the stylet in the stylet lumen so as to align such bend in the stylet with one of the flexible spacer portions so as to change the angle of at least a portion of the lead, and further moving the lead within the patient in a second direction different from the first direction.

BRIEF DESCRIPTION OF THE DRAWINGS

The numerous advantages of the present invention may be better understood by those skilled in the art by reference to the accompanying drawings in which.

BEST MODE(S) FOR CARRYING OUT THE INVENTION

The following description is of a particular embodiment of the invention, set out to enable one to practice an implementation thereof, and is not intended to limit the preferred embodiment, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

Figure 1:
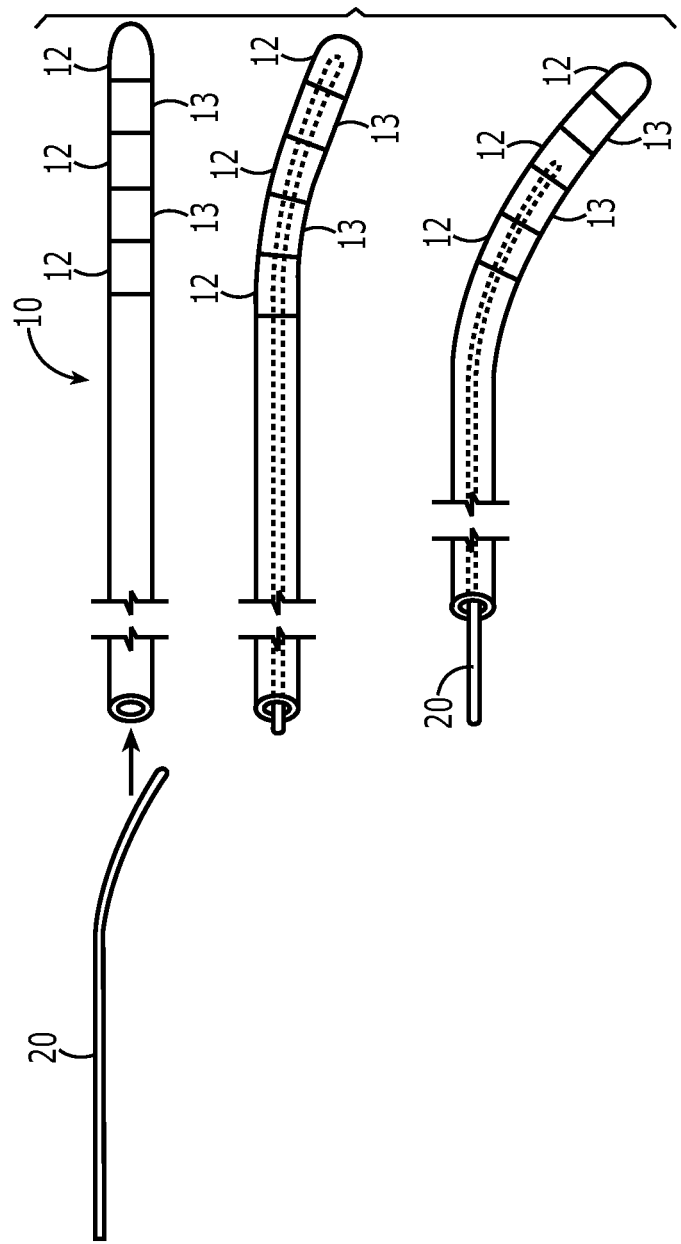
FIG. 1 is a side view of a prior art multi-contact lead and a bent stylet engaging such lead.
Figure 2:
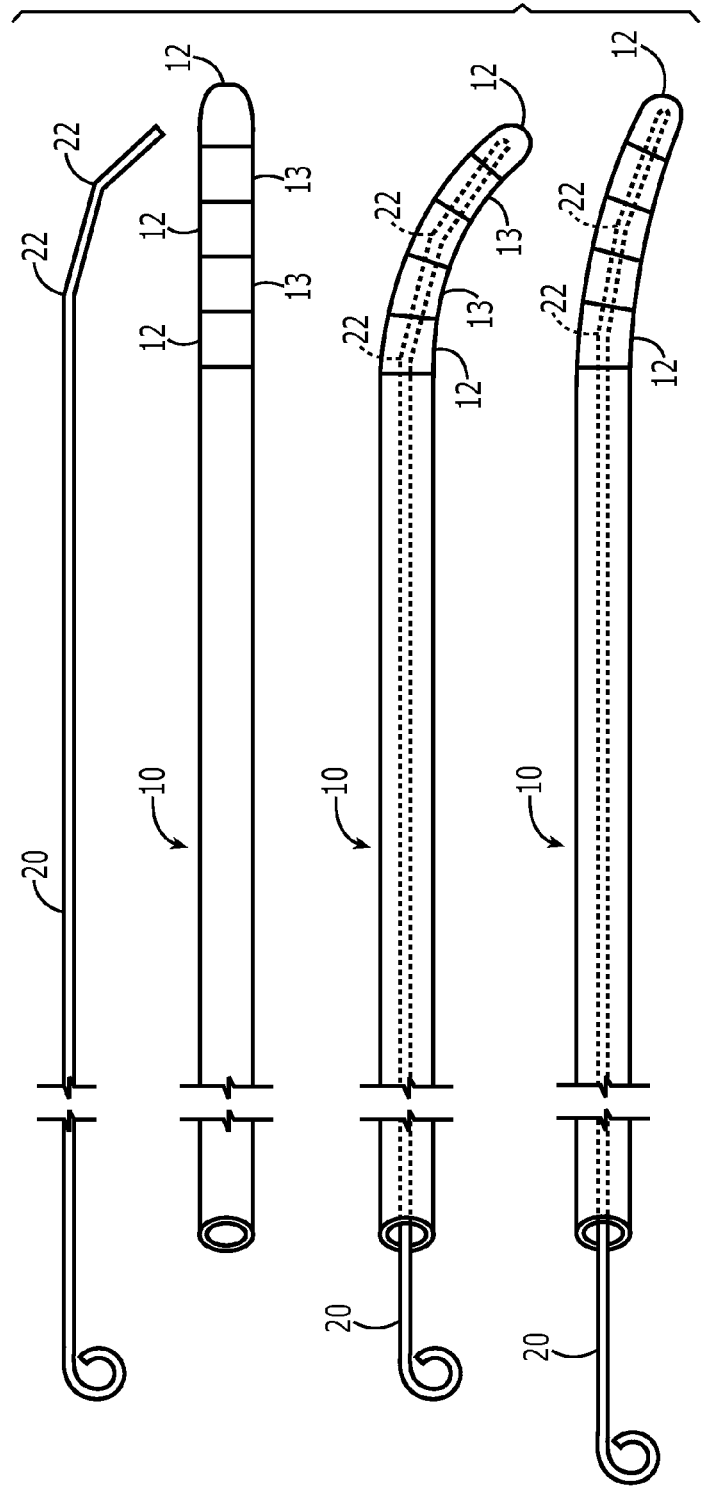
FIG. 2 is a side view of a system comprising a multi-contact lead and stylet according to certain aspects of a particularly preferred embodiment of the invention.

As shown in FIG. 2, a flexible lead 10 comprising a multicontact electrode is provided with an electrode array having rigid electrode contacts 12 separated by flexible spacer portions 13, typically of uniform length. A stylet 20 is also provided which, when such stylet is inserted into flexible lead 10, is configured to cause the lead 10 to bend. As the stylet 20 is advanced within flexible lead 10, lead 10 will conform to the stylet 20 and the bend will advance. To the extent that the lead is inflexible, it will not conform to the bend in the stylet, and in the extreme case in which it is completely rigid, e.g. a cylindrical electrode contact of sufficient length, within which the stylet is constrained by the inside diameter, it will not bend at all.

In accordance with one aspect of an embodiment of the invention, stylet 20 is provided preferably multiple focal bends 22, which are relatively acute (i.e., having a relatively small radius or curvature), with relatively straight (i.e., having a large to infinite radius of curvature) segments between focal bends 22, the dimensions of which are preferably chosen so that one or more of the bends may be made to line up with the flexible spacer portions 13 when the stylet is inserted to just the right depth of flexible lead 10. This will cause the tip of the electrode array to bend to the maximum degree, as shown in the middle illustration of FIG. 2. When the stylet 20 is moved to a position in which its bends are within the rigid electrode contacts 12 and its relatively straight sections are within the flexible spacer portions 13, this reduces the bend in the array to a minimum, as shown in the bottom illustration of FIG. 2.

As shown in FIG. 2, bends 22 (two are shown in FIG. 2) may be positioned so as to lie within flexible spacer portions 13 of lead 10, causing the lead 10 to bend, or within a rigid segments, in this case the electrode contacts 12, minimizing the resulting bend in lead 10. Although a single bend will create a bending effect, the exemplary embodiment depicted in FIG. 2 shows two bends 22 in series, with identical and complementary spacing of electrode contacts and flexible spacer portions, so that the effects are cumulative or additive. When the bends in stylet 20 are in phase with the flexible spacer portions 13, the assembly bends; when they are out of phase with the flexible spacer portions 13, the assembly straightens.

The phase of one or more bends 22 in stylet 20 with respect to the flexible spacers and the rigid electrode contacts of the electrode array, as its longitudinal position is varied, determines the magnitude of the bend of the assembly.

Although the contacts 12 and flexible spacer portions 13 are of uniform length in the exemplary embodiment depicted in FIG. 2, such that the spacing between stylet bends 22 is equal to the sum of one contact and one spacer length, this need not be the case. Those of ordinary skill in the art will recognize that there are multiple possible variations in the lengths of each of these elements that may allow the rigid and flexible elements to interact with the bends in the stylet so as to increase or reduce the curvature of the assembly at one or more points along its length. Common to all is the interaction of the relatively acute stylet bend with the relatively flexible spacer at one or more points. Also common to all, and a benefit of the instant invention, is the ability to vary the bend in a flexible lead 10 (in particular at or near the tip, within or near the electrode contacts 12) by moving the stylet 20 within the lead 10, without changing its bend, removing it, or replacing it, resulting in significant convenience for the operator.

Figure 3:
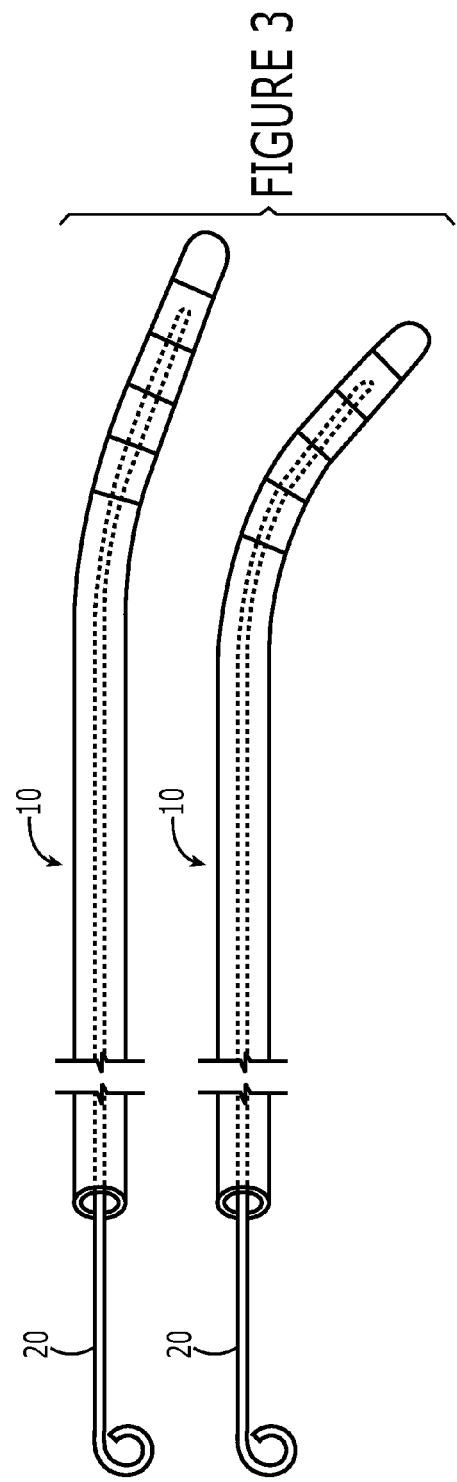
FIG. 3 is a side view the system of FIG. 2 showing the effect of varied flexibility of portions of a lead on bending of the lead.

In accordance with another aspect of a preferred embodiment of the invention, and with particular regard to FIG. 3, flexible lead 10, or specific portions thereof, may be provided in varying degrees of flexibility, which in turn will affect the extent to which stylet 20 will cause flexible lead 10 to bend when it is inserted into lead 10. As shown in FIG. 3, the flexible lead shown in the top illustration is less flexible than the flexible lead shown in the bottom illustration. As a result, when an identically bent stylet 20 is inserted in either of the two flexible leads 10 shown in FIG. 3, the more flexible conforms more readily to the bend in the stylet 20, approaching the angle of the original bend in the stylet 20, while the more rigid lead 10 bends less.

Figure 4:
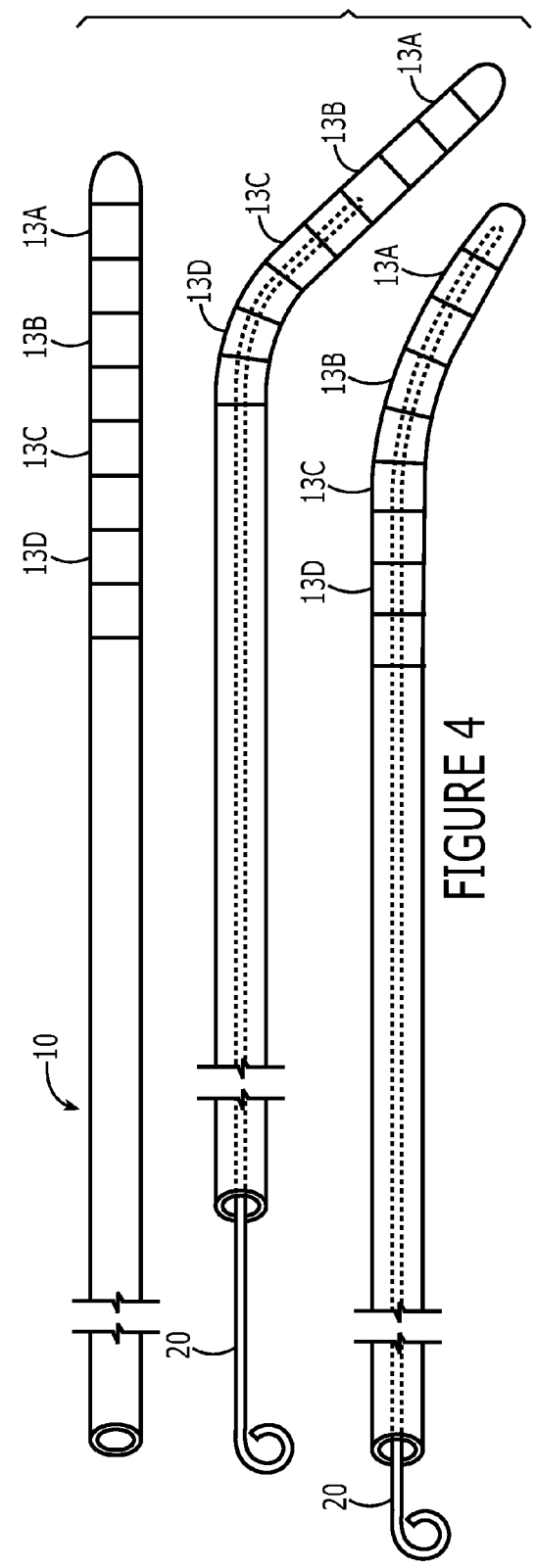
FIG. 4 is a side view of the system of FIG. 2 showing further effects of varied flexibility of portions of a lead on bending of the lead.

Next, as shown in FIG. 4, a single flexible lead 10 may be provided with segments of different flexibility. In the exemplary embodiment shown in FIG. 4, the two spacer portions 13A and 13B nearest the tip of the electrode are more stiff (less flexible), and the two spacer portions 13C and 13D further from the tip are less stiff (more flexible). Thus, as stylet 20 with a particular given bend is advanced into flexible lead 10, when the bend encounters the more flexible spacer portions 13C and 13D, the lead 10 bends maximally. When the stylet 20 is advanced further into the more rigid spacer portions 13A and 13B at the tip of the lead 10, the bend is minimal.

Those of ordinary skill in the art will thus recognize from the foregoing that the flexibility of spacer portions 13 in a flexible lead 10, as well as the flexibility of the electrode contacts 12 (as discussed in more detail below), may be varied at any position along the length of the lead 10, giving any particular segment more or less overall flexibility. A stylet bend traversing this segment will cause the lead 10 to bend correspondingly more or less. Thus, a wide variety of flexible lead configurations may be provided whose varying degrees of flexibility may be particularly well suited for specific applications. As shown in FIG. 4, two relatively stiff spacer portions 13A and 13B and two relatively flexible spacer portions 13C and 13D may be used with presumably stiff electrode contacts 12, although this is merely one possible example, and the numbers of electrode contacts and spacer portions, and their flexibility, may vary without departing from the spirit and scope of the invention.

Once again, a benefit of the instant invention is to allow the operator to vary the bend in the lead by simply repositioning the stylet 20 within flexible lead 10, instead of requiring the operator to, for instance, remove and reconfigure the bend and thereafter attempt to replace the stylet 20 within the lead 10. In the particular example shown in FIG. 4, the operator may use the maximum bend to negotiate the sharp turn at the tip of the needle entering the epidural space, and then advance the stylet 20 within the lead to reduce the bend for finer steering adjustments as the procedure continues. This allows the operator to vary the bend at the tip of the lead 10 by simply moving the stylet 20 longitudinally a small amount. This avoids the cumbersome process of withdrawing the stylet 20 from the lead 10 to change its bend.

Relatively small radius bends are shown in the representative Figures for illustrative purposes. In practice, those of ordinary skill in the art will recognize that the radius of the bend should be large enough, and the stylet 20 should be flexible enough, to advance and withdraw through the inside diameter of the lead 10. Those of ordinary skill in the art will also find it beneficial to mark or index the stylet 20 and/or the lead to indicate their relative positions (visibly and/or palpably), and in some applications to secure the stylet with respect to the lead to maintain their relative positions, as discussed in greater detail below.

Figure 5:
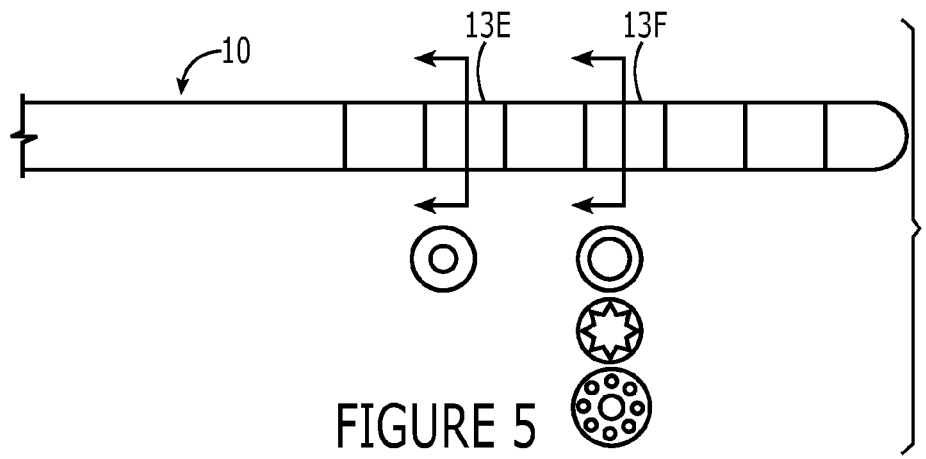
FIG. 5 is a side and various cross-sectional views of the lead of FIG. 2 with varied configurations of flexible spacer portions.

Next, FIG. 5 shows various configurations for altering the flexibility of spacer portions 13 in lead 10. A typical lead segment 13E consists of a cylindrical tube or catheter segment. However, the flexibility of any given catheter segment may be modified in a number of ways. First, the configuration of the lead segment may be varied without changing materials (as shown in optional cross-sectional views of segment 13F) by relieving or removing portions of the inner wall, such as by adding grooves or ridges, or substituting another form of the same material such as foam, to reduce durometer and increase flexibility, by comparison with a full thickness wall. Moreover, the materials of which a spacer segment is comprised may be modified, such as by using material of different durometer, such as silicone elastomer instead of polyurethane. Still further, materials may be combined, for example silicone elastomer inside of polyurethane, or for example adding stiffening elements, which may simply resist bending or may function as tension or compression elements in a beam, as shown at the bottom illustration of FIG. 5. Wires (which may or may not function as electrical conductors) or stylets may be added as well to vary flexibility.

Figure 6:
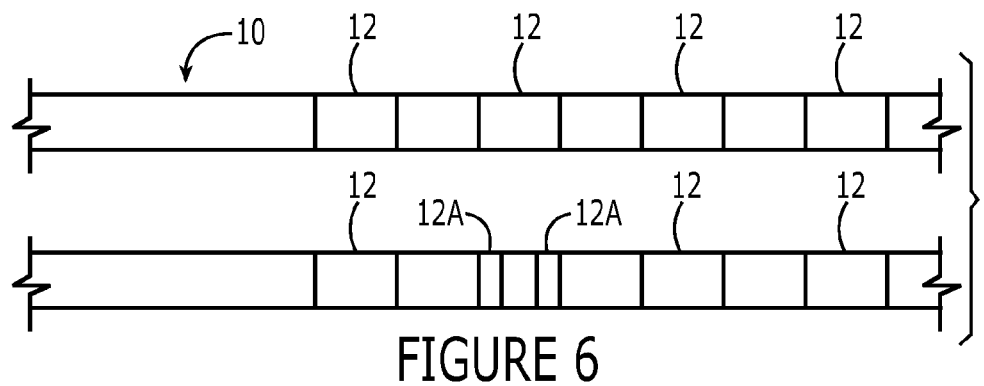
FIG. 6 is a side view of the lead of FIG. 2 with a segmented electrode contact.

Moreover, and with reference to FIG. 6, flexibility of electrode contacts 12 may likewise be modified. In the example shown in FIG. 6, this may be accomplished by segmenting electrode contacts 12. Where a series of N electrode contacts 12 are provided in a linear array, one such contact at a particular distance from the tip of the lead 10 (i.e., where increased flexibility is desired) may be replaced with n (two or more) shorter electrode contacts 12A, the lengths of which preferably sum to less than the length of the original electrode contact 12. The difference in length is made up by flexible spacer portions separating the shorter electrode contacts (for purposes of this example, although not necessarily or in general, as lengths may vary). If the electrode contacts 12A are connected in parallel, together they will constitute a single virtual electrode contact, the position of which will be equivalent to that of the larger electrode contact 12. Local current density at the individual segments will be a bit higher, but current density will be the same several millimeters away, e.g., at the spinal cord. Impedance will be a bit higher, as well. The virtual electrode contact will preferably have the same length as the original electrode contact, and so the uniformity of electrode contact spacing by comparison with the original can be preserved.

The individual electrode contact segments could optionally be connected to the generator individually, and programmed as such, increasing spatial resolution, but current density would be much higher (at least n times higher, exceeding n to the extent flexible spacer portions replace contact surface). The segments could be distinguished as N1, N2, etc., and would occupy the position originally occupied by electrode contact N.

As noted above, the multiple short electrode contact segments 12A are preferably connected in parallel, i.e., wired together, for example with spiral conductors, to function as one longer contact with internal flexibility, giving this segment of a multicontact array more flexibility.

While not shown explicitly in the drawings, it is also envisaged that the joints between electrode contacts 12 and spacer portions 13 may themselves also be flexible, and such flexibility may be varied, for the same purposes as described above.

Figure 7:
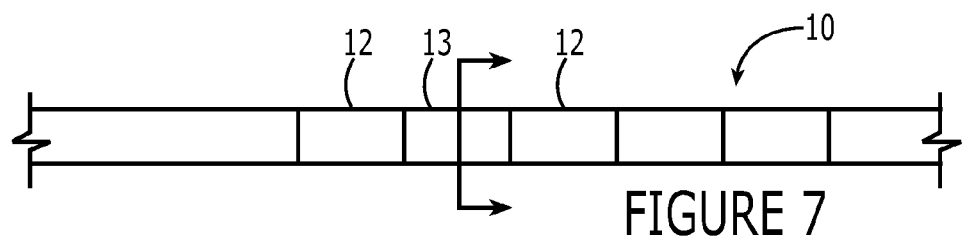
FIG. 7 is a side and various cross-sectional views of the lead of FIG. 2 with further varied configurations of flexible spacer portions.
Figure 7A:
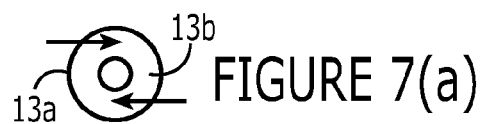
Figure 7B:
Figure 8:
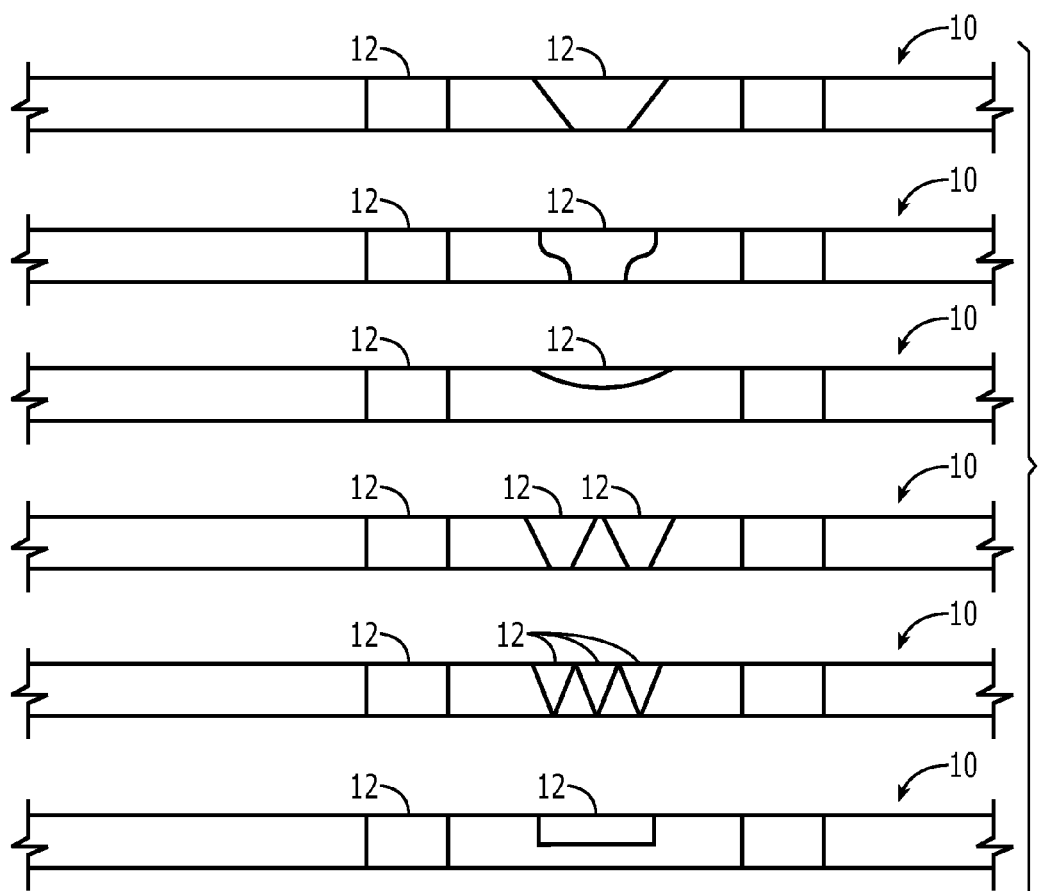
FIG. 8 is a side, cross-sectional view of the lead of FIG. 2 depicting various configurations of asymmetric spacer portions and electrode contacts.
Figure 9A:
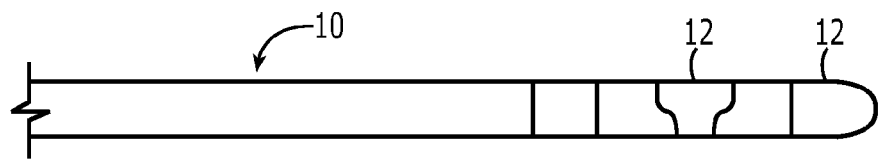
FIG. 9 is a side view of certain lead configurations of FIG. 8 showing the effect of such configurations when subjected to bending from a bent stylet.
Figure 9B:
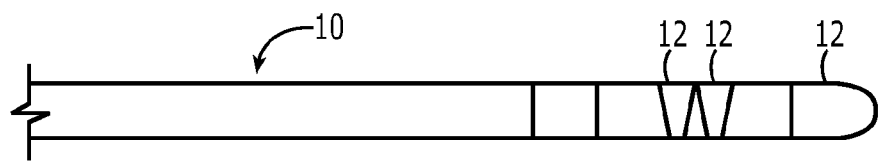
Figure 9C:
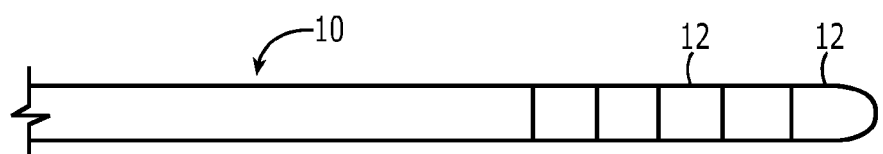
Figure 9D:
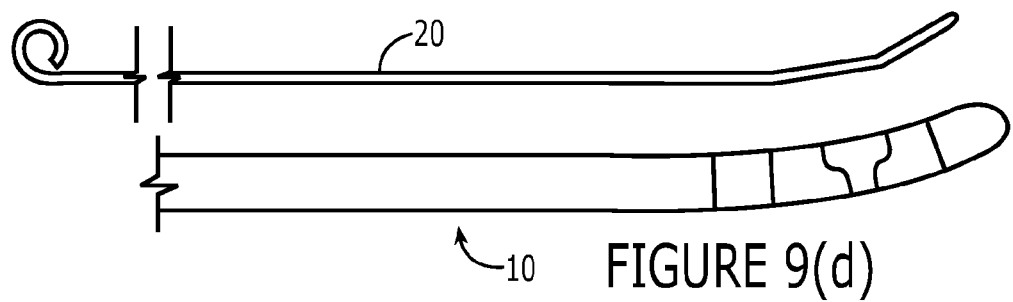
Figure 9E:
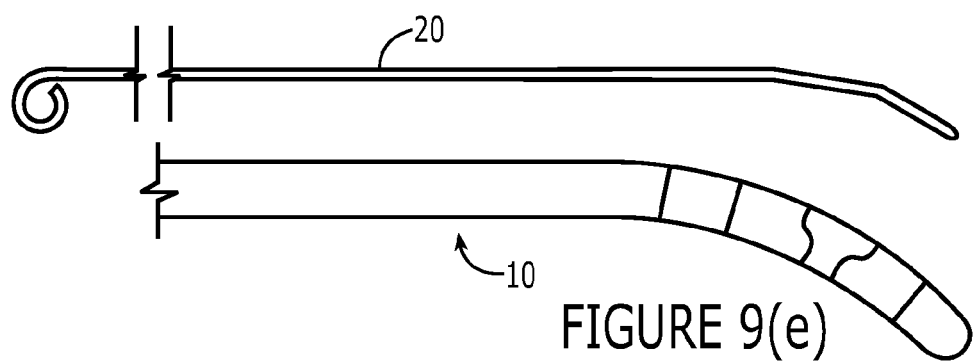

Next, as shown in FIG. 7, radial asymmetry may also be used to vary the flexibility of segments of lead 10. More particularly, while all commercially available percutaneous electrode contacts known to the inventor herein are cylindrical, and thus in cross-section are radially symmetric, FIG. 7 shows the general case of an asymmetrical spacer, and FIG. 8 shows specific examples of variously asymmetrically configured spacers and electrode contacts, which may be used to alter the flexibility of segments of lead 10.

As shown in FIG. 7, by constructing a lead 10 so that, as seen in the cross-sectional view of illustration (a) of FIG. 7, one side 13A is of lower durometer than the other side 13B, then it will bend more readily toward this lower durometer side. Thus, if the bend in a stylet is toward the low durometer side 13A, the assembly will bend maximally; if it is turned 180 degrees, toward the high durometer side 13B, it will bend minimally. The concept of "phase" as discussed above may be introduced again, this time radially: the stylet may be rotated so that the bend is in phase with the preferred bend of the lead, for maximal bending of the assembly. It may be rotated 180 degrees out of phase for minimal bending. It may be rotated to intermediate positions for intermediate bending.

As shown in FIG. 7, the asymmetric cross-section of the lead 10 may be achieved in a number of different ways, to the same effect. If the stylet lumen (which may be considered as the inside diameter of a single lead catheter or as one catheter inside another) is concentric with the outside of the lead, then the materials on one side and/or the other may be chosen to resist tension or compression, achieving the requisite asymmetry. If the stylet lumen is off-center, as shown in illustration (b), so that the wall thickness varies from one side to the other, this confers asymmetry. In practice, there will be at least one electrical conductor within the lead, all the way to the tip contact; and there will be more and more proximally, to serve additional electrode contacts; these conductors can be arranged so that they function as mechanical elements, to confer asymmetry.

As was the case with the longitudinally phased example described above, the radially phased example of FIG. 7 allows the bend at the tip of lead 10 to be varied by small movements of the stylet 20; in this case, rotary movements. Once again, this avoids the need to re-bend, remove, or replace the stylet 20.

Similarly, such asymmetric cross-section of lead 10 may be achieved by way of wedge-shaped electrode contacts and complementary intervening flexible, compressible plastic (e.g., polyurethane) spacer portions, examples of which are shown in the various cross-sectional views of FIG. 8, which by virtue of the longer compressible segments between the shorter side(s) of the contact segment(s) allow the assembly to bend more easily in this direction, to a greater (more acute) angle. This will facilitate steering when a more pronounced bend is needed, e.g., when the electrode array first emerges from the end of a Tuohy needle into the dorsal spinal epidural space.

As used here, the term "wedge" refers generically to a shape which, as seen from either side, is longer at one edge and shorter at the other edge. The sloping contour from one edge to the other may be straight, curved, sawtooth, etc. The term "wedge" should also be considered to encompass shapes in which the height at one edge is zero, and even one in which there is a gap, so that the contact does not encircle the full 360 degree circumference of the catheter.

Turning a bent stylet 180 degrees within the body of lead 10, thus reversing its direction and causing the bend to reverse, will cause equal and symmetric bending of the electrode assembly if the contacts and spacers are cylindrical and of uniform material. If, on the other hand, wedges are provided in lead 10 as generally shown in FIG. 8, rotating the bent stylet tip toward the side or edge with the shorter portion of metallic electrode contact segments 12 and the longer compressible plastic spacer portions will allow a more pronounced bend, as this side is more compressible.

Rotating the stylet 180 degrees so that the bent tip is toward the shorter plastic spacer portions and the longer electrode contact segments will result in a less pronounced bend, as this side of the assembly is less compressible, thus providing for a straighter tip for more subtle steering, as when nearing target level. Intermediate angles of rotation will produce intermediate bends. All of such varied bends in lead 10 may be accomplished without requiring that the operator withdraw or replace the stylet.

It is noted that ancillary benefit may be had by providing contacts in such wedge-shaped configurations beyond providing controlled curvature of lead 10 in response to radial movement of a stylet within such lead. More particularly, the narrow part of a wedge may still function as an electrode; thus, in spinal cord stimulation applications, if the narrow side of the wedge-shaped electrode contact is placed towards the dura, and the wider part toward the ligamentum flavum, this will reduce local current density and thus may reduce painful side effects. Moreover, the wedge electrode contacts on a cylindrical catheter may provide it the attributes of a "percutaneous paddle," while being forgiving of inverted placement.

Next, as shown in FIG. 9, various configurations of electrode contacts 12 are shown. In illustrations (a) and (b), electrode contact configurations are shown that are visibly (and thus radiographically) asymmetric, while in illustration (c), electrode contact configurations are shown that are not visibly asymmetric. Regardless, common to each such configuration is the visible change in bend as the stylet is rotated in and out of phase, as depicted in the bottom two illustrations of FIG. 9. More particularly, as shown in illustration (d) of FIG. 9, as stylet 20 is rotated in lead 10 to an out of phase orientation, a minimal bend results in lead 10. In contrast, as shown in illustration (e) of FIG. 9, as stylet 20 is rotated in lead 10 to an in phase orientation, a maximum bend results in lead 10. Notably, whether the leads 12 are visibly asymmetric or not, the bend that results in lead 10 when stylet 20 is rotated is radiographically visible, thus aiding the operator in maintaining proper orientation during insertion of the lead 10.

Figure 10:
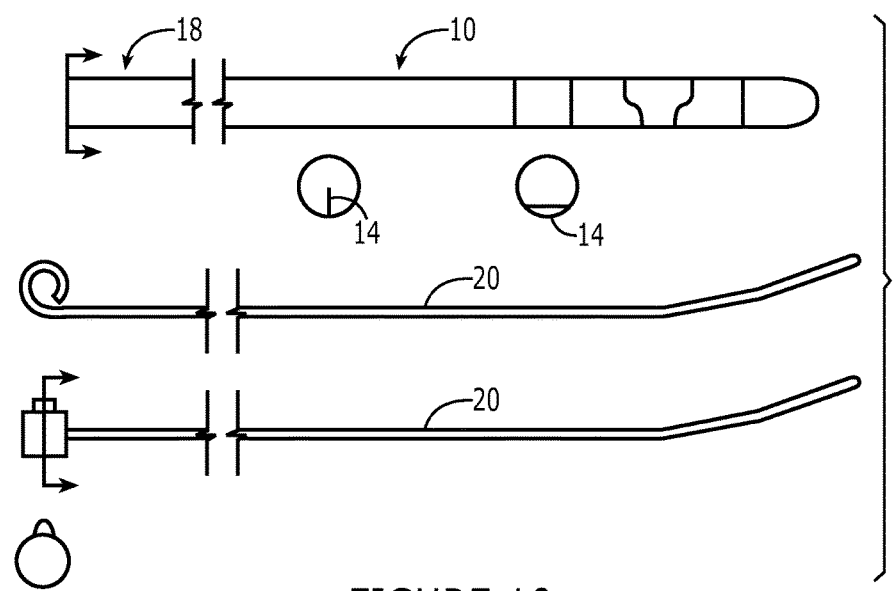
FIG. 10 is a side view of the lead of FIG. 2 showing various configurations for indexing a stylet and an associated lead.

As shown in FIG. 10, in order to further assist the operator in maintaining proper orientation during insertion of the lead 10, the radial position of a stylet with respect to lead 10 may be indexed. Rotation of a stylet 20 within lead 10, as well as rotation of the two together or separately, may be significant with the radially asymmetric designs shown herein. Thus, a point or radial position 14 on the circumference of the connector end 18 of the lead may be marked, where it is visible to and palpable by the operator. Similarly, as shown in the bottom illustrations of FIG. 10, the handle (or knob or loop) on the stylet may be marked to indicate the direction of the bend in stylet 20. In the exemplary illustration of FIG. 10, there is a loop at the back end of stylet 20 (the end manipulated by the operator) which points in the same direction as the bend in the front end or tip of stylet 20.

In use, and by way of non-limiting example, the bent stylet 20 may be inserted into the radially asymmetric lead "in phase" to achieve the maximal bend. The operator would pass the assembly through the Tuohy needle with the bend directed left or right as appropriate. The bend (and perhaps wedges, if present) will be visible in profile as the electrode tip emerges from the tip of the needle and negotiates the turn out of the needle, which is the most difficult corner of all. The stylet may then be rotated out of phase with the lead as a smaller bend is required thereafter.

It is believed that the present invention and many of its attendant advantages will be understood by the forgoing description. It is also believed that it will be apparent that various changes may be made in the form, construction and arrangement of the components thereof without departing from the spirit and scope of the invention or without sacrificing all of its material advantages. The form herein before described is merely an explanatory embodiment thereof.

INDUSTRIAL APPLICABILITY

The present invention is applicable to surgical medical devices and related methods. The invention discloses an electrode and stylus and related method configured for aiding in the placement of such electrode at a desired location within a patient's body. The device can be made in industry and practiced in the medical field.

I claim:

1. A system for positioning a lead within a patient, comprising:

a lead comprising a shaft having a plurality of electrode contacts disposed thereon and a flexible spacer portion between each of said electrode contacts, said shaft having a section defining a cylindrical exterior wall, which section includes at least one of said electrode contacts and at least one of said flexible spacer portions, which section has a uniform outer diameter along the length of the section, and a stylet lumen extending into said lead from a proximal end thereof towards a distal end thereof, wherein one or more planar cross-sections through said lead taken in a direction perpendicular to a major axis extending lengthwise through a center of said lead and through said section defining a cylindrical exterior wall include a portion of said at least one electrode contact and a portion of said at least one flexible spacer portion, and wherein said portion of said at least one electrode contact is asymmetrically positioned with respect to said major axis in said one or more planar cross-sections; and a stylet having a plurality of bends therein and relatively straight portions extending between said bends, wherein said bends are positioned a distance apart from one another so as to simultaneously align with said flexible spacer portions of said lead when said stylet is positioned within said stylet lumen;

wherein a first one of said flexible spacer portions has greater flexibility than a second one of said flexible spacer portions, such that one of said bends in said stylet engaging said first one of said flexible spacer portions will cause said lead to bend at a larger angle than said one of said bends in said stylet engaging said second one of said flexible spacer portions.

2. The system of claim 1, wherein said first one of said flexible spacer portions comprises a cylindrical wall having a first thickness, and a second flexible spacer portion comprises a cylindrical wall having a second thickness that is greater than said first thickness.

3. The system of claim 1, wherein said first one of said flexible spacer portions is formed of a first material, and said second flexible spacer portion is formed of a second material, wherein said first material has a greater flexibility than said second material.

4. The system of claim 1, said second flexible spacer portion further comprising at least one stiffening insert embedded within said second flexible spacer portion.

5. The system of claim 1, wherein at least a first one of said electrode contacts has a first length L, and at least two second electrode contacts each have a second length that is less than L/2, and wherein said first flexible spacer portion is positioned between said first one of said electrodes and one of said second electrodes, and said second flexible spacer portion is positioned between said at least two second electrodes.

6. The system of claim 5, wherein a combined length of two of said second electrodes and said second flexible spacer portion equals L.

7. The system of claim 1, wherein said system is configured such that aligning said one of said bends in said stylet with said first one of said flexible spacer portions will cause said lumen to bend at an angle, and rotation of said stylet within said stylet lumen when said one of said bends in said stylet is aligned with said first one of said flexible spacers will cause the magnitude of said angle to vary.

8. The system of claim 7, wherein said first one of said flexible spacer portions further comprises a cylindrical section formed of compressible material having a top side and a bottom side opposite said top side, and wherein said top side has a first durometer rating and said bottom side has a second durometer rating different from said first durometer rating.

9. The system of claim 7, wherein said first one of said flexible spacer portions further comprises a cylindrical section formed of compressible material, and wherein said stylet lumen extends through said first one of said flexible spacer portions along an axis that is set off from a central axis of said at least one flexible spacer portion.

10. The system of claim 7, wherein at least one of said electrode contacts is radially asymmetric such that a first side of said at least one electrode contact is of a greater length than a second side of said at least one electrode contact opposite said first side, and wherein said first one of said flexible spacer portions is adjacent said at least one electrode and has a radially asymmetric configuration that is complementary to said at least one electrode contact.

11. The system of claim 7, said stylet further comprising an indicia configured to indicate both a radial orientation and a longitudinal orientation of said stylet with respect to said stylet lumen.

12. A method of using the system of claim 1, comprising the steps of:
    inserting said stylet into said stylet lumen toward said distal end of said lead a sufficient distance so that at least one of said bends in said stylet is aligned with at least one of said electrode contacts;
    moving said lead within a patient in a first direction;
    moving said stylet in said stylet lumen so as to align said one of said bends in said stylet with one of said flexible spacer portions so as to change the angle of at least a portion of said lead; and
    further moving said lead within said patient in a second direction different from said first direction.

13. The method of claim 12, further comprising the steps of:
    further moving said stylet in said stylet lumen toward said distal end of said lead so as to further change the angle of at least a portion of said lead; and
    further moving said lead within said patient in a third direction different from said second direction.

14. The method of claim 12, wherein said step of moving said stylet in said stylet lumen further comprises rotating said stylet within said stylet lumen.

15. The method of claim 14, wherein rotation of said stylet within said stylet lumen causes a magnitude of an angle to which said lead is bent to vary.

* * * * *